United States Patent [19]

Schmidhammer et al.

[11] Patent Number: 4,584,123

[45] Date of Patent: Apr. 22, 1986

[54] PROCESS FOR UPGRADING HYDROGEN CHLORIDE CONTAINING CHLORINE, IRON-III-CHLORIDE, ETHYLENE AND/OR ACETYLENE

[75] Inventors: Ludwig Schmidhammer, Haiming; Gerhard Dummer, Burgkirchen; Klaus Haselwarter; Rudolf Strasser, both of Burghausen, all of Fed. Rep. of Germany

[73] Assignee: Wacker-Chemie GmbH, Munich, Fed. Rep. of Germany

[21] Appl. No.: 633,965

[22] Filed: Jul. 24, 1984

[30] Foreign Application Priority Data

Oct. 10, 1983 [DE] Fed. Rep. of Germany ....... 3336816

[51] Int. Cl.⁴ .................... C09K 3/00; C07C 17/156
[52] U.S. Cl. ................. 252/188.31; 570/243; 570/244; 570/245
[58] Field of Search .......... 252/188.31; 570/243, 570/244, 245

[56] References Cited

U.S. PATENT DOCUMENTS

| 4,071,572 | 1/1978 | Amato et al. | 570/243 |
| 4,346,069 | 8/1982 | Riegel et al. | 570/243 X |
| 4,351,819 | 9/1982 | Riegel et al. | 570/243 X |

Primary Examiner—John F. Terapane
Assistant Examiner—Matthew A. Thexton
Attorney, Agent, or Firm—Collard, Roe & Galgano, P.C.

[57] ABSTRACT

A process of upgrading hydrogen chloride which contains chlorine, iron-III-chloride, acetylene and/or ethylene, for use in an oxichlorination process, wherein water in a gaseous state is added to the hydrogen chloride at temperatures between 120° and 180° C. within a time period of maximally 0.9 seconds after the acetylene and/or ethylene is present in the hydrogen chloride, together with chlorine and iron-III-chloride.

2 Claims, No Drawings

PROCESS FOR UPGRADING HYDROGEN CHLORIDE CONTAINING CHLORINE, IRON-III-CHLORIDE, ETHYLENE AND/OR ACETYLENE

The present invention relates to a process for upgrading hydrogen chloride containing chlorine and iron-III-chloride, as well as ethylene and/or acetylene, for use in an oxichlorination process.

Hydrogen chloride is used in large amounts for the production of 1,2-dichloroethane by oxichlorination of ethylene. This hydrogen chloride may be derived from different sources and contains, depending on its origin, various impurities. Hydrogen chloride obtained by the thermal cracking of dichloroethane to form vinyl chloride always contains small amounts of acetylene or its hydrogenation product ethylene. Hydrogen chloride derived from chlorination reactions in which substitution takes place, e.g., from chlorination of acetic acid or aromatics, or from perchlorination of $C_1$ to $C_3$ hydrocarbons, always contains elementary chlorine. The same is true of hydrogen chloride obtained in the combustion of chlorinated hydrocarbons, e.g. the combustion of chlorinated hydrocarbon distillation residues.

Since hydrogen chloride is usually passed through pipelines of steel, hydrogen chloride contaminated with chlorine contains at all times at least small amounts of iron chloride formed by the corrosion of steel by chlorine. This phenomenon occurs in the continuous operation of a plant even though the hydrogen chloride has previously undergone a conventional purification step to remove chlorine, e.g., a washing with carbon tetrachloride or an adsorptive purification with activated carbon filters. After such purification steps, there are always small amounts of chlorine present-namely, in the amount of a two-digit ppm range.

If, therefore, chlorine-containing and therewith iron-III-chloride-containing hydrogen chloride is fed into the preliminary heating step of an oxichlorination process and is mixed with ethylene or acetylene derived from whatever source (at least when, as conventionally done, pipelines of steel are used), within a short time of operation, soot or coke-like decomposition products are deposited on the lines, on measuring devices, and, finally, on the catalyst bed of the oxichlorination catalyst.

The consequences are well known: upsets of plant operations; the risk of explosions due to faulty measurements, deactivation of the oxichlorination catalyst; an increase of pressure drop across the catalyst bed, and the like.

It is therefore the object of the invention to provide a process by which the above-mentioned disadvantages, particularly the formation of soot and coke deposits, are avoided.

It has now been found that the addition of water in the form of steam to hydrogen chloride containing chlorine and iron-III-chloride, as well as ethylene or acetylene, will accomplish this object.

Thus, the present invention relates to a process for upgrading hydrogen chloride containing chlorine and iron-III-chloride, as well as ethylene and/or acetylene, the process being characterized by adding gaseous water at temperatures between 120° and 180° C. within a period of maximally 0.9 seconds after acetylene and/or ethylene, as well as chlorine and iron-III-chloride, are present in the hydrogen chloride, the amount of water being 5–20 mole % with reference to the total amount of the hydrogen chloride.

The hydrogen chloride to be treated according to the invention contains chlorine in amounts of 20 vol.-ppm to 200 vol.-ppm, especially 30 vol.-ppm to 80 vol.-ppm, in each case referring to the total volume of hydrogen chloride, and amounts of iron-III-chloride of 1–4 mg per $Nm^3$. If the above mentioned amounts of chlorine and iron-III-chloride are exceeded, the hydrogen chloride is subjected to a prior conventional purification step, e.g., by passing the hydrogen chloride over an activated carbon filter, or by washing it in carbon tetrachloride, or purifying the hydrogen chloride in azeotropically boiling hydrochloric acid, and the like.

The amounts of acetylene are, as a rule, not higher than the ones obtained as a by-product in the cracking process of 1,2-dichloroethane, i.e., about 0.05–0.5 vol. %, when the hydrogen chloride is derived from such sources.

The amounts of ethylene vary within wide limits ranging from the amounts mentioned above for acetylene to about the total quantity of ethylene necessary for the oxichlorination.

According to the invention, temperatures between 120° and 180° C. are maintained, which are necessary for the preheating of the reaction mixture for the oxichlorination process, as well as for avoiding a drop below the dew point.

The amount of water used as steam is 5 to 20 Mole % referring to the total amount of hydrogen chloride undergoing oxichlorination. It is stressed once more that the water used in the system according to the invention has to be exclusively in the gaseous state. The addition of steam occurs, at the latest, 0.9 seconds, and preferably between 0.3 and 0.8 seconds, after chlorine, and therewith iron-III-chloride, as well as the above mentioned amounts of acetylene and/or ethylene are present in the hydrogen chloride. The reaction mixture is maintained at a temperature of at least 120° C.

Since the operational steps according to the invention serve to prepare hydrogen chloride for an oxichlorination, the steam is advantageously added to the system together with the necessary amount of oxygen or the corresponding air flow. Alternatively, the addition of steam can be carried out via the ethylene flow or the ethylene and/or acetylene containing gas flow. It goes without saying that the addition of steam can occur separately as long as the time periods of maximally 0.9 seconds are maintained.

The so prepared mixture is finally introduced into the oxichlorination system.

By following the procedure according to the invention, it is possible to keep the feed pipes to the oxichlorination system, as well as the oxichlorination catalyst, free of soot and coke deposits.

In the following, the invention will be more fully described in a number of examples, but it should be understood that these are given by way of illustration and not of limitation.

EXAMPLE 1

100 kmoles/h of hydrogen chloride from a perchlorination plant having a content of 30 vol.-ppm chlorine and 5 mg $FeCl_3$ per $Nm^3$ were passed over a bed of activated carbon at 20° C. Then the hydrogen chloride was preheated to 170° C. while being passed over a steel heat exchanger. At the exit from the heat exchanger, the hydrogen chloride contained 30 vol.-ppm of chlorine and 1.5 mg FeCl$_3$ per Nm$^3$. Thereafter, the preheated hydrogen chloride was mixed with 55 kmoles/h of ethylene preheated to 40° C. Immediately afterwards a mixture was added containing 54 kmoles/h of steam, the mixture being preheated to 180° C. The time period of the reaction mixture between ethylene addition and air/steam addition was 0.3 seconds. The so prepared vapor mixture finally flowed toward a fixed-bed oxichlorination plant consisting of three reactors arranged in series. The additionally required 80 kmoles/h of air for a quantitative reaction of hydrogen chloride with ethylene to form 1,2-dichloroethane was added between the first and second reactor and the second and third reactor.

The activity of the catalyst did not decrease after one year of operation. No soot- or coke-like deposits could be detected at the inlet or inside of the reactor.

COMPARISON EXAMPLE 1

The operation of Example 1 was repeated with the modification that no steam was added to the reaction system. After standing for two months, a compression of the catalyst bed was found in the first reactor caused by pressure drop increase. At the same time, an undesired by-product formation of ethyl chloride and vinyl chloride was detected and a decrease in the conversion rate of hydrogen chloride in the oxichlorination process. After six months of operation the plant had to be shut down due to too high pressure drop in the first reactor.

COMPARISON EXAMPLE 2

The operation of Example 1 was repeated with the modification that the time period between the mixing of ethylene with hydrogen chloride and the addition of the air/steam mixture was 1 second.

After the plant had operated for 9 months, the catalyst in the first reactor had to be changed, because the amount of coke-like deposits was so large that it caused an increase in the pressure drop across that reactor which was no longer tolerable.

EXAMPLE 2

110 kmoles/h of hydrogen chloride from a perchlorination plant were passed over a bed of activated carbon. The chlorine content was at that time 50 vol.-ppm, the FeCl$_3$ content 1.2 mg per Nm$^3$. The hydrogen chloride was preheated to 155° C. and mixed with 300 kmoles/h of hydrogen chloride that came from a 1,2-dichloroethane-cracking plant and contained 2000 vol.-ppm of ethylene, 400 vol.-ppm of ethane, and 10 vol.-ppm of acetylene. The hydrogen chloride from the cracking process had a temperature of 160° C. The mixture was mixed with 235 kmoles/h of ethylene. Then a mixture of 226 kmoles/h of air and 45 kmoles/h of steam was added in such a manner that the time period between the first addition of ethylene or acetylene, respectively, and the addition of steam was 0.75 seconds. Finally, the system was passed on to an oxichlorination reactor.

After the plant had been in operation for 18 months, there were no deposits of coke in the pipelines of the combined hydrogen chloride flows or within the first reactor.

COMPARISON EXAMPLE 3

The operation of Example 2 was repeated with the modification that the time period between the first ethylene addition to the hydrogen chloride obtained from the perchlorination process and the steam addition was 1.5 seconds.

After one month of operation, there already were coke deposits detected on a measuring orifice, which was in the pipeline system of the combined hydrogen chloride flows.

While only a few examples and embodiments of the present invention have been described, it is obvious that many changes and modifications may be made thereunto, without departing from the spirit and scope of the invention.

What is claimed is:

1. A method for making a composition for use in the oxychlorination of ethylene, comprising the steps of:
    (a) combining hydrogen chloride containing small amounts of chlorine and of iron III chloride with a member selected from the group consisting of (i) hydrogen chloride containing acetylene or ethylene or mixtures thereof, (ii) ethylene and (iii) mixtures thereof;
    (b) then adding water in the vapor state in an amount of 5 to 20 mole % relative to the total amount of hydrogen chloride, at a temperature of between 120° C. and 180° C. within a time period of maximally 0.9 seconds after step (a).

2. The process of claim 1, wherein said time period is between 0.3 and 0.8 seconds.

* * * * *